United States Patent
Sameshima et al.

(10) Patent No.: US 9,634,229 B2
(45) Date of Patent: Apr. 25, 2017

(54) PIEZOELECTRIC DEVICE, ULTRASOUND PROBE, DROPLET DISCHARGE DEVICE, AND PIEZOELECTRIC DEVICE FABRICATION METHOD

(71) Applicant: KONICA MINOLTA, INC., Chiyoda-ku (JP)

(72) Inventors: Kouichi Sameshima, Kyoto (JP); Takashi Matsuo, Suita (JP)

(73) Assignee: KONICA MINOLTA, INC., Tokyo (JP)

( * ) Notice: Subject to any disclaimer, the term of this patent is extended or adjusted under 35 U.S.C. 154(b) by 270 days.

(21) Appl. No.: 14/383,465

(22) PCT Filed: Feb. 12, 2013

(86) PCT No.: PCT/JP2013/000743
§ 371 (c)(1),
(2) Date: Sep. 5, 2014

(87) PCT Pub. No.: WO2013/132747
PCT Pub. Date: Sep. 12, 2013

(65) Prior Publication Data
US 2015/0057540 A1    Feb. 26, 2015

(30) Foreign Application Priority Data

Mar. 8, 2012  (JP) ................. 2012-051349

(51) Int. Cl.
*H01L 41/08* (2006.01)
*B06B 1/06* (2006.01)
(Continued)

(52) U.S. Cl.
CPC ............... *H01L 41/08* (2013.01); *B06B 1/06* (2013.01); *B41J 2/14201* (2013.01);
(Continued)

(58) Field of Classification Search
CPC ....... A61B 8/4405; A61B 8/4483; B06B 1/06; B41J 2/14233; H01L 41/08; H01L 41/257
(Continued)

(56) References Cited

U.S. PATENT DOCUMENTS

| | | | |
|---|---|---|---|
| 6,051,910 A * | 4/2000 | Kaida | H03H 9/178 310/320 |
| 6,222,304 B1 | 4/2001 | Bernstein | |
| 6,232,698 B1 * | 5/2001 | Kaida | H03H 9/0207 310/320 |
| 6,460,979 B1 | 10/2002 | Heinzl et al. | |
| 6,967,432 B2 * | 11/2005 | Mitani | H03H 9/177 310/320 |
| 2004/0232803 A1 | 11/2004 | Matsushita et al. | |

(Continued)

FOREIGN PATENT DOCUMENTS

| | | |
|---|---|---|
| JP | 62-105600 | 5/1987 |
| JP | 2005-5698 | 1/2005 |

(Continued)

*Primary Examiner* — Jaydi San Martin
(74) *Attorney, Agent, or Firm* — Cozen O'Connor

(57) ABSTRACT

In a piezoelectric device, an ultrasound probe, and a droplet discharge unit of the present invention, each of a pair of first and second electrodes is placed on a piezoelectric member having a single orientation in a direction perpendicular to a thickness direction thereof to extend in a direction perpendicular to the thickness direction or along the thickness direction and in a direction perpendicular to the direction of the orientation. Therefore, the piezoelectric device of the present invention has excellent piezoelectric properties. Further, the ultrasound probe and the droplet discharge unit of the present invention have good efficiency.

17 Claims, 13 Drawing Sheets

(51) Int. Cl.
*H01L 41/09* (2006.01)
*H01L 41/316* (2013.01)
*B41J 2/14* (2006.01)
*H01L 41/35* (2013.01)
*H01L 41/047* (2006.01)
*H01L 41/187* (2006.01)
*H01L 41/313* (2013.01)
*A61B 8/00* (2006.01)

(52) U.S. Cl.
CPC ........ *B41J 2/14233* (2013.01); *H01L 41/047* (2013.01); *H01L 41/0475* (2013.01); *H01L 41/0973* (2013.01); *H01L 41/1876* (2013.01); *H01L 41/313* (2013.01); *H01L 41/316* (2013.01); *H01L 41/35* (2013.01); *A61B 8/4405* (2013.01); *A61B 8/4483* (2013.01); *B41J 2002/14491* (2013.01); *Y10T 29/42* (2015.01)

(58) Field of Classification Search
USPC ........................................................ 310/357
See application file for complete search history.

(56) References Cited

U.S. PATENT DOCUMENTS

| | | | |
|---|---|---|---|
| 2010/0073823 A1* | 3/2010 | Aoki | G11B 5/6005 360/291.9 |
| 2010/0109489 A1 | 5/2010 | Matsushita | |
| 2010/0117750 A1* | 5/2010 | Fry | H03H 9/02086 331/162 |
| 2014/0167571 A1* | 6/2014 | Meyer | H01L 41/107 310/366 |
| 2015/0179921 A1* | 6/2015 | Asano | H01L 41/0472 310/357 |
| 2016/0211776 A1* | 7/2016 | Ting | H02N 2/001 310/323.16 |

FOREIGN PATENT DOCUMENTS

| | | |
|---|---|---|
| JP | 2008-288453 | 11/2008 |
| JP | 2011-143047 | 7/2011 |
| WO | WO 02/071504 | 9/2002 |

* cited by examiner

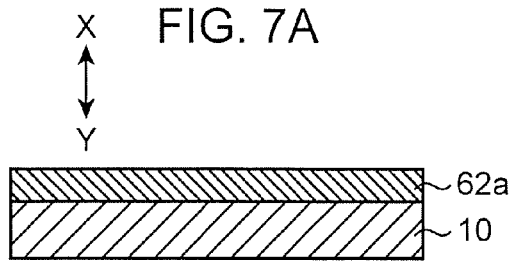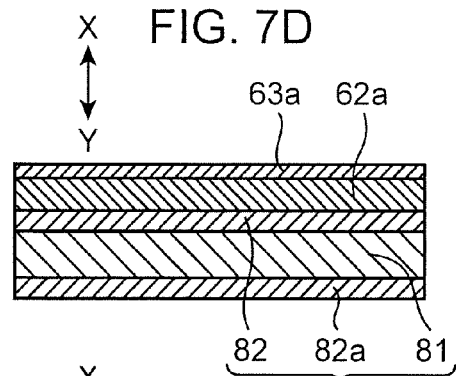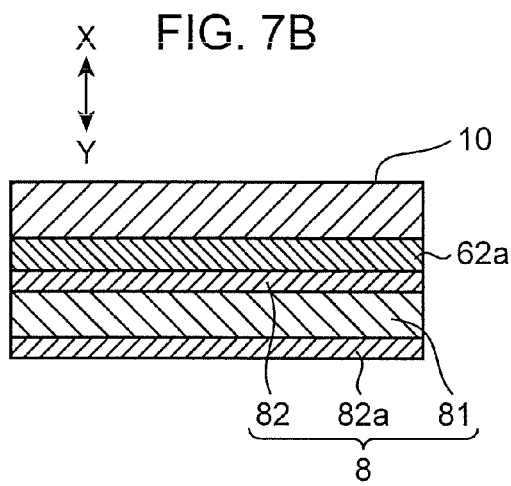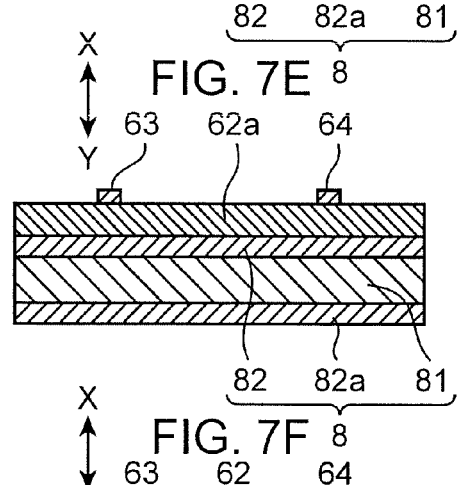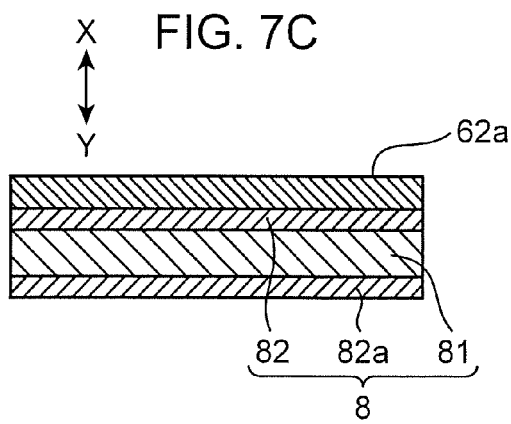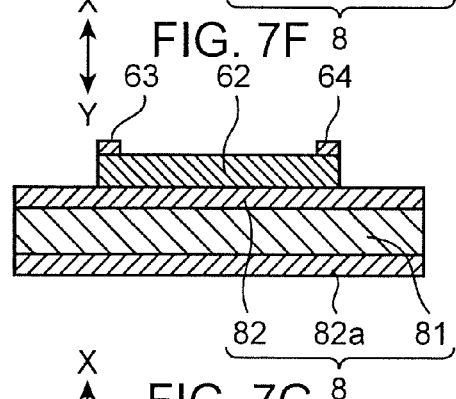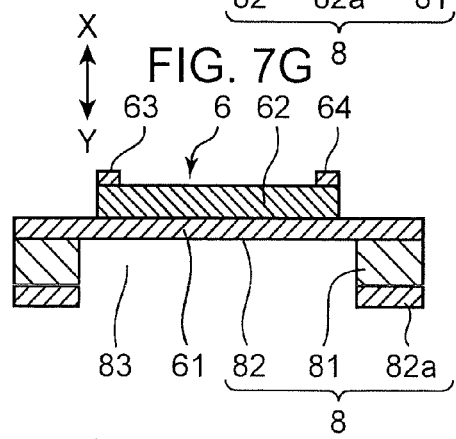

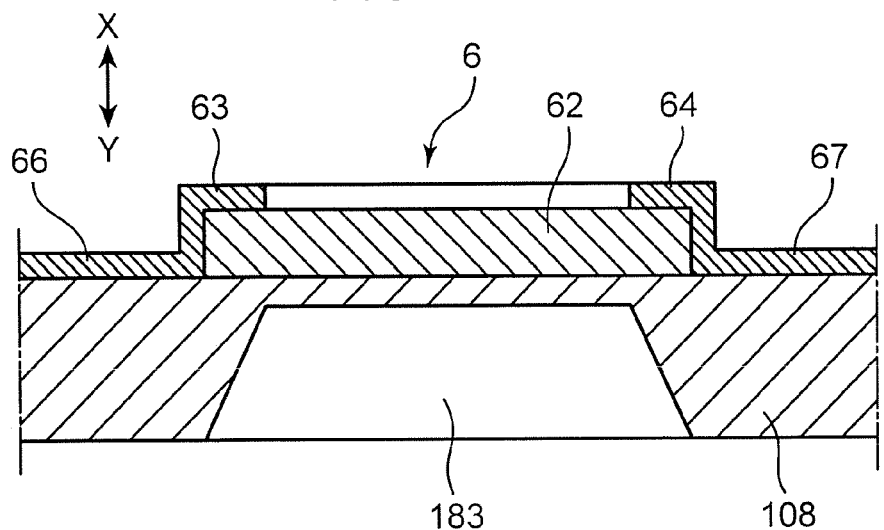
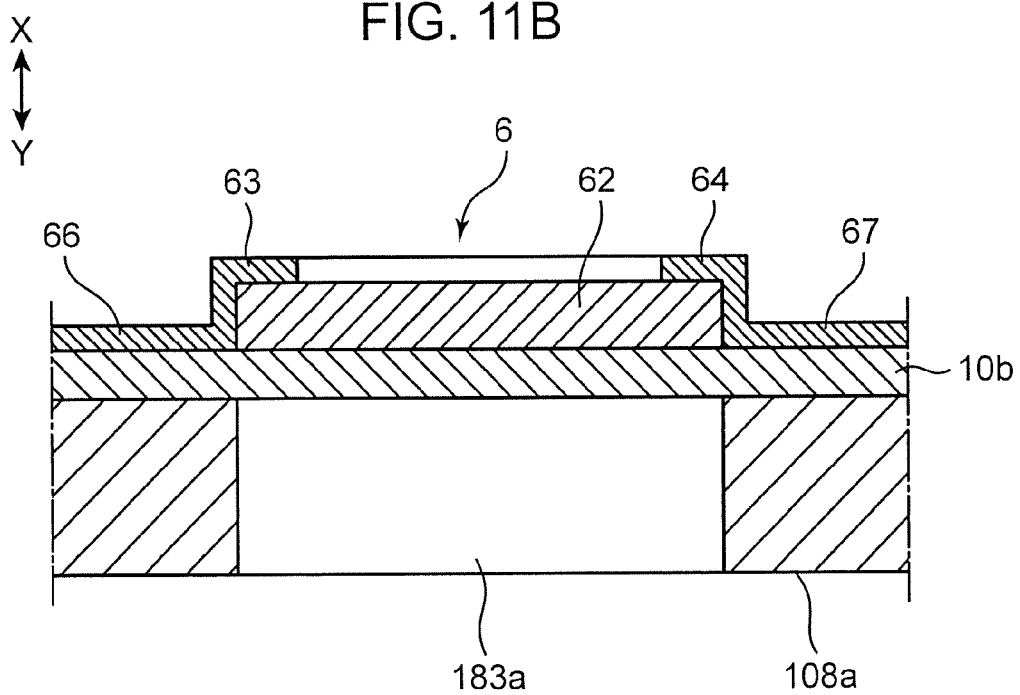

PIEZOELECTRIC DEVICE, ULTRASOUND PROBE, DROPLET DISCHARGE DEVICE, AND PIEZOELECTRIC DEVICE FABRICATION METHOD

RELATED APPLICATIONS

This is a U.S. National stage of International application No. PCT/JP2013/000743 filed on Feb. 12, 2013.

This patent application claims the priority of Japanese application no. 2012-051349 filed Mar. 8, 2012 the disclosure content of which is hereby incorporated by reference.

TECHNICAL FIELD

The present invention relates to a piezoelectric device, an ultrasound probe, a droplet discharge unit, and a piezoelectric device fabrication method.

BACKGROUND ART

A scene where an ultrasonic diagnostic apparatus diagnosis is applied to medical diagnosis has been increasing, because it has feature of being able to perform observation of body tissues in a non-invasive manner and on a real-time basis. In such an ultrasonic diagnostic apparatus, there has been known a pMUT (Piezoelectric Micromachined Ultrasonic Transducer) configured to vibrate, like a drumhead, a diaphragm having a unimorph structure in which a piezoelectric member made of PZT or the like is formed on a substrate, to thereby perform transmitting and receiving of ultrasound.

As compared to a transducer using a piezoelectric member obtained by dividing a bulk PZT material into pieces by dicing, the pMUT-type ultrasound probe has advantages of being able to broaden a frequency band, and promote miniaturization of an element to achieve higher resolution, and of being suited to achieving a two-dimensional array of diaphragms (vibrators) for acquiring a three-dimensional image, and applying to an ultrasound endoscope because of its ability to promote reductions in size and thickness. On the other hand, in a one-dimensional array of diaphragms, an acquirable image is limited to a tomographic image, and thereby a false-negative result is likely to occur depending on operation, so that an operator (medical doctor, ultrasound diagnostic technician) is required to have a certain level of proficiency. For this reason, there is a high need for a two-dimensional array type ultrasound probe capable of acquiring a three-dimensional image.

This type of ultrasound probe is configured to perform energy conversion in the following manner. During transmitting, it is operable to convert electric energy to mechanical energy (vibration of diaphragms), and further convert the mechanical energy to acoustic energy (ultrasound). During receiving, it is operable to convert acoustic energy (ultrasound) to mechanical energy (vibration of diaphragms), and further convert the mechanical energy to electric energy.

In the conversion between mechanical energy and acoustic energy, acoustic matching is important, and it is a point for design to match an effective acoustic impedance of the pMUT with an acoustic impedance of a living body. In the conversion between electric energy and mechanical energy, it is important to enhance energy conversion efficiency of a diaphragm structure including a piezoelectric member. A piezoelectric member becomes most efficient (in an index representing performance of a piezoelectric member, k-value: electromechanical coupling coefficient becomes higher), when utilizing a strain in the same direction (33 direction) as a direction of electric field, so that an ultrasound probe advantageously employs a configuration using a strain in the 33 direction. This configuration allows an inter-electrode distance to be set to a relatively large value, as compared to a configuration in which each electrode is placed to extend in a thickness direction of a PZT-based piezoelectric member, so that there is a merit of being able to improve sensitivity (output voltage to unit pressure) during receiving of ultrasound.

As this type of ultrasound probe utilizing a strain in the 33 direction, there has been known an element having a structure illustrated, for example, in FIG. 17. This element has a thin film-shaped diaphragm d which comprises: a ring plate-shaped piezoelectric member a; a ring-shaped plus electrode b placed on an upper surface, i.e., one surface in a thickness direction, of the piezoelectric member a, at a position radially inward of the piezoelectric member a; and a ring-shaped minus electrode c placed radially outward of the plus electrode b, and the diaphragm d is held by a holding member e. When the element having this structure is driven, electricity is supplied to the pair of plus electrode b and minus electrode c to thereby radially apply an electric field in the 33 direction which is a direction (radial direction) perpendicular to the thickness direction of the piezoelectric member a. Thus, in this element, the piezoelectric member a is strained in the radial direction (deformed in the 33 direction), and, according to this unimorph effect, the diaphragm d is bendingly deformed like a drumhead, to thereby transmit ultrasound.

As the type utilizing a strain in the 33 direction, a micro-shell transducer is disclosed, for example, in the following Patent Literature 1. In this transducer, a piezoelectric member (solid electro-active medium) is laminated on a holding support substrate in such a manner as to form a diaphragm (arched section) inside two shoulder sections, and a pair of electrodes are mounted, respectively, on the shoulder sections, wherein a chamber is formed between the diaphragm and the holding substrate. Then, a voltage is applied along a direction from a plus one of the electrodes to the other, minus, electrode, and thereby an electric field is generated in the same direction. Thus, in this transducer, a stress is induced in the piezoelectric member in the same direction, and, as a result, the diaphragm is moved upwardly or downwardly in a thickness direction thereof, i.e., bendingly deformed in a curved shape.

Meanwhile, in such a diaphragm, if an orientation direction of a piezoelectric member is not coincident with a poling direction, it is hard to expect improvement in piezoelectric properties.

In the structure illustrated in FIG. 17 where the ring-shaped electrodes are placed to utilize a stress in the 33 direction, i.e., a direction perpendicular to the thickness direction, when a poling treatment is performed by applying a relatively strong voltage between the pair of electrodes, a poling direction is radially oriented, so that an orientation direction of the unpoled piezoelectric member a becomes different from the poling direction, resulting in difficulty in improving piezoelectric properties.

More specifically, for example, when the piezoelectric member a is formed on a single-crystal substrate having lattice constants close to those of the piezoelectric member a, the piezoelectric member a can be formed to have a single orientation along one of the thickness direction thereof and a direction perpendicular to the thickness direction (e.g., along the V-V direction in FIG. 17). Even using such a piezoelectric member a having a single orientation, a piezoelectric device utilizing a piezoelectrically-induced stress in a 31 direction, i.e., the thickness direction, can have highly-improved piezoelectric properties, because the orientation direction becomes identical to a poling direction, whereas, in the ring-shaped electrodes placed to utilize a stress in the 33 direction, i.e., a direction perpendicular to the thickness direction, an area where the orientation direction of the piezoelectric member a is different from the poling direction (radial direction) increases, resulting in difficulty in improving piezoelectric properties.

In the Patent Literature 1, a relationship between an orientation direction and a poling direction is not disclosed at all, and it cannot be exactly said that the transducer has excellent piezoelectric properties.

CITATION LIST

Patent Literature

Patent Literature 1: U.S. Pat. No. 6,222,304 B

SUMMARY OF INVENTION

The present invention has been made in view of the above circumstances, and an object thereof is to provide a piezoelectric device having excellent piezoelectric properties, and a production method for the piezoelectric device. It is another object of the present invention is to provide an ultrasound probe and a droplet discharge unit each using the piezoelectric device.

According to a piezoelectric device, an ultrasound probe and a droplet discharge unit of the present invention, a pair of first and second electrodes are placed on a piezoelectric member, wherein the piezoelectric member has a single orientation in a direction perpendicular to a thickness direction thereof, and the first and second electrodes extend in the direction perpendicular to the thickness direction and in a direction perpendicular to the direction of the orientation. Alternatively, the first and second electrodes may be placed to extend in a direction along the thickness direction and in a direction perpendicular to the direction of the orientation. Thus, the piezoelectric device of the present invention has excellent piezoelectric properties. Further, each of the ultrasound probe and the droplet discharge unit of the present invention has good efficiency.

These and other objects, features, and advantages of the present invention will become apparent upon reading of the following detailed description along with the accompanying drawings.

BRIEF DESCRIPTION OF DRAWINGS

FIG. 7 illustrates a production process of the ultrasound transmitting-receiving section, wherein FIGS. 7A to 7G are sectional explanatory diagrams of steps of the production process.

FIG. 11A is a fragmentary enlarged sectional view of a first example of modification of the ultrasound transmitting-receiving section, and FIG. 11B is a fragmentary enlarged sectional view of a second example of the modification of the ultrasound transmitting-receiving section.

DESCRIPTION OF EMBODIMENTS

Based on the drawings, one embodiment of the present invention will now be described. Elements or components assigned with the same reference sign in the figures mean that they are identical, and therefore duplicated description thereof will be omitted appropriately. In this specification, when a term collectively means a plurality of identical elements or components, it is designated by a reference sign without any suffix, whereas, when the term means a specific one of the elements or components, it is designated by the reference sign with a suffix.

Figure 1:
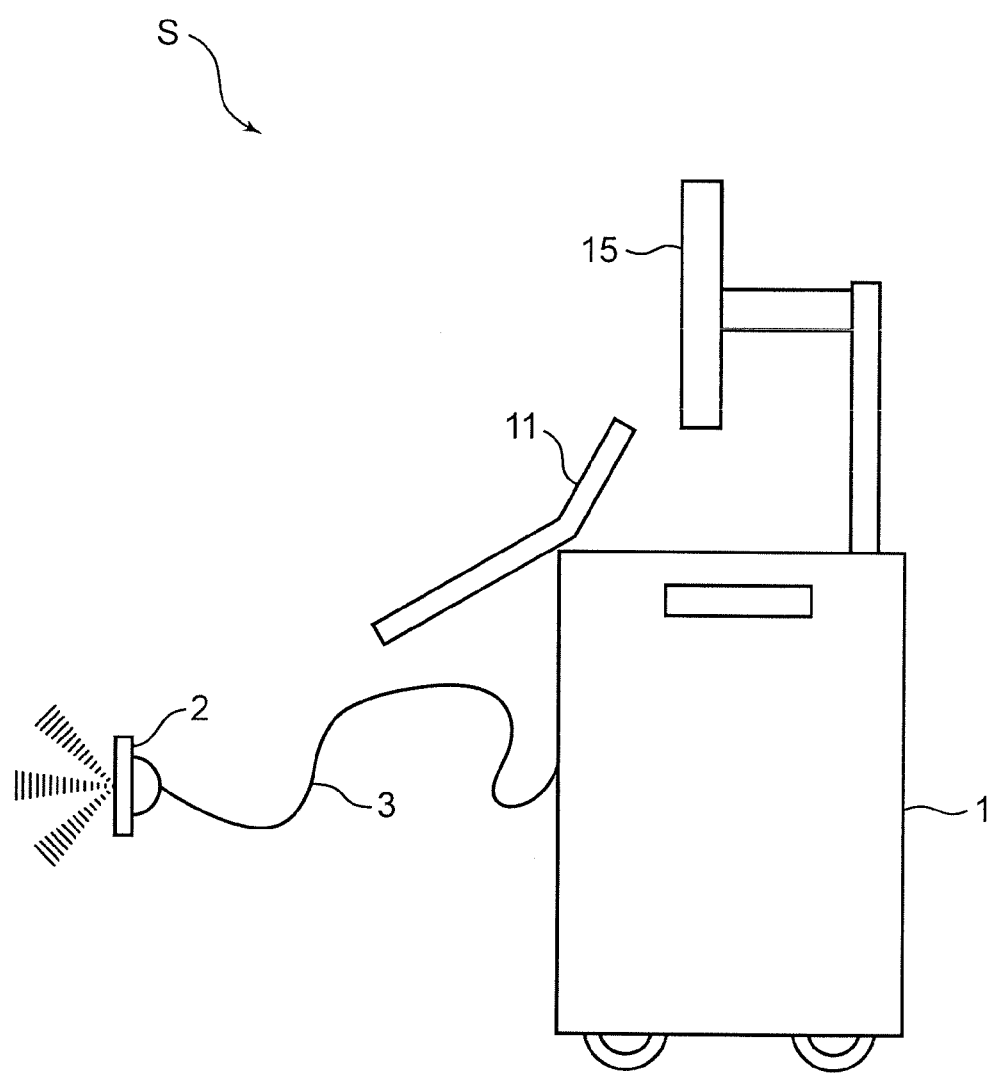
FIG. 1 is a diagram illustrating a configuration of an external appearance of an ultrasound diagnostic apparatus having an ultrasound probe according to a first embodiment of the present invention.
Figure 2:
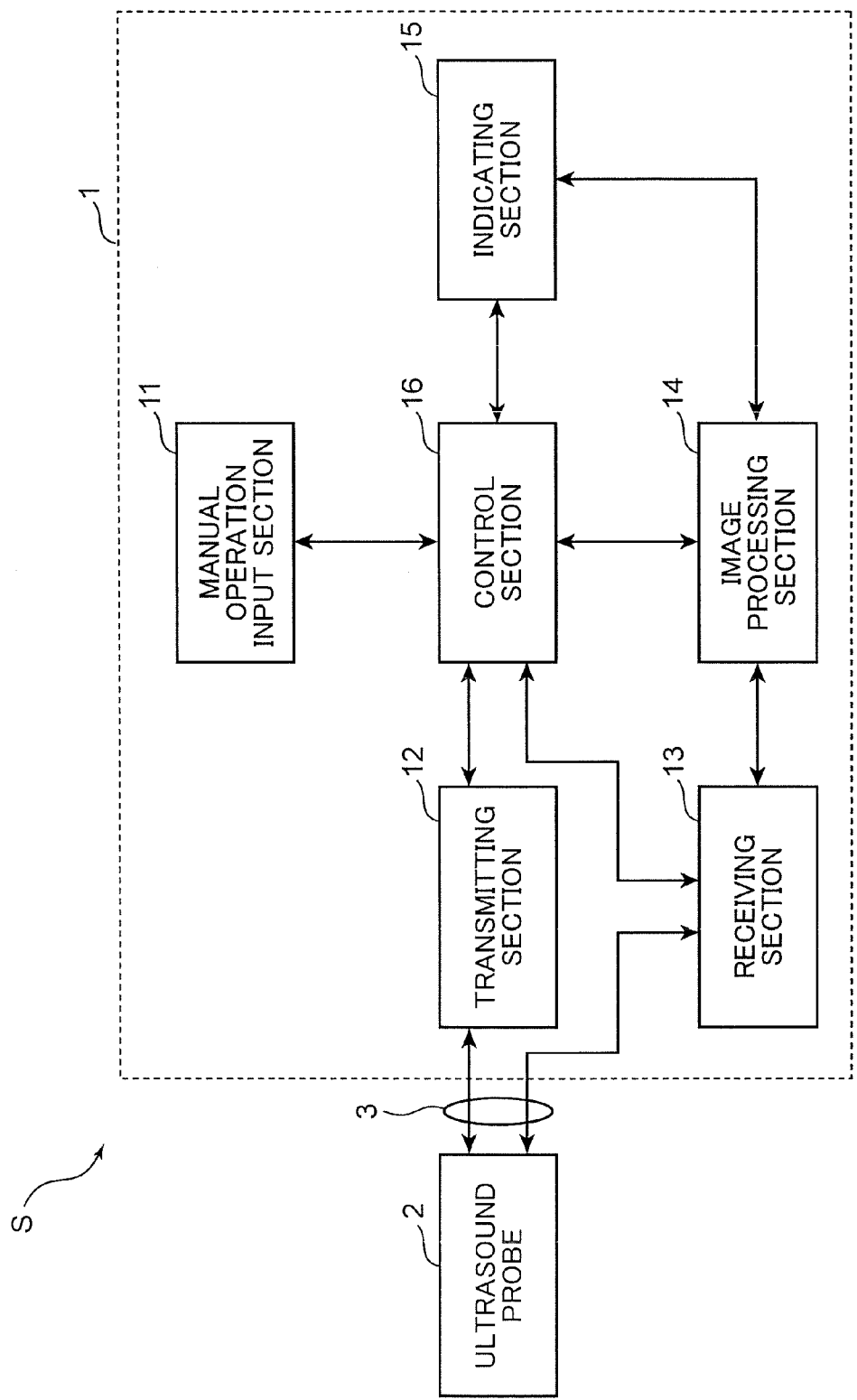
FIG. 2 is a block diagram illustrating an electrical configuration of the ultrasound diagnostic apparatus having the ultrasound probe.
Figure 3:
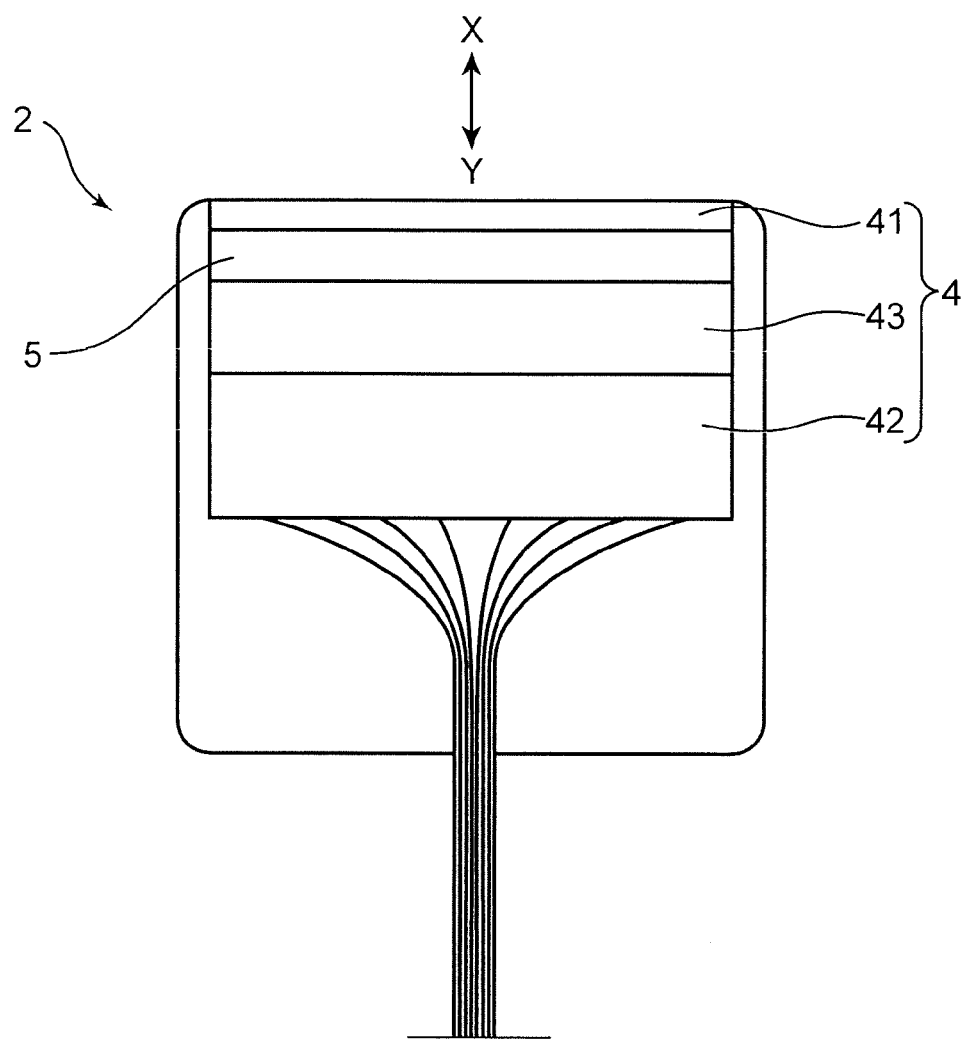
FIG. 3 is a sectional view illustrating a configuration of the ultrasound probe in the ultrasound diagnostic apparatus.

FIG. 1 is a diagram illustrating a configuration of an external appearance of an ultrasound diagnostic apparatus having an ultrasound probe according to a first embodiment. FIG. 2 is a block diagram illustrating an electrical configuration of the ultrasound diagnostic apparatus having the ultrasound probe according to the first embodiment. FIG. 3 is a sectional view illustrating a configuration of the ultrasound probe according to the first embodiment.

The ultrasound diagnostic apparatus S in the first embodiment has an apparatus main unit 1, and the ultrasound probe 2. The ultrasound probe 2 is configured to transmit ultrasound (a first ultrasound signal) to an illustration-omitted subject such as a living body, and receive ultrasound (a second ultrasound signal) coming from an inside of the subject in accordance with the first ultrasound signal. The apparatus main unit 1 is connected to the ultrasound probe 2 via a cable 3, and configured to send a transmitting signal in the form of an electric signal, to the ultrasound probe 2 via the cable 3 to thereby instruct the ultrasound probe 2 to transmit the first ultrasound signal to the subject, and image an internal state of the subject in the form of an ultrasound image, based on a receive signal generated by the ultrasound probe 2 in the form of an electric signal, according to the second ultrasound signal coming from the inside of the subject and received by the ultrasound probe 2.

The ultrasound coming from an inside of the subject in accordance with the first ultrasound signal includes not only a reflected wave (echo) generated as a result of a phenomenon that the first ultrasound signal is reflected by mismatch between acoustic impedances in the inside of the subject, but also, in the case where an ultrasound contrast agent (contrast medium) such as microbubbles is used, ultrasound generated by microbubbles as the ultrasound contrast agent in accordance with the first ultrasound signal. In the ultrasound contrast agent, upon irradiation with ultrasound, microbubbles as the ultrasound contrast agent resonate, and, at a sound pressure of a given threshold or more, break up and disappear. In the ultrasound contrast agent, in conjunction with resonance of the microbubbles, or breaking/break up and disappearance of the microbubbles, ultrasound is generated.

For example, as illustrated in FIG. 2, the apparatus main unit 1 has a manual operation input section 11, a sending section 12, a receiving section 13, an image processing section 14, an indicating section 15, and a control section 16.

For example, the manual operation input section 11 is a device configured to allow an user to input a command for giving instruction on start of diagnosis or the like and data such as personal information of a subject, and composed of an operation panel having a plurality of input switches, a keyboard or the like.

For example, the sending section 12 is configured to send a control signal from the control section 16, to the ultrasound probe 2. For example, the receiving section 13 is configured to receive the receive signal transferred from the ultrasound probe 2, and output the receive signal to the image processing section 14.

The image processing section 14 is a circuit configured to, under control of the control section 16, form an image (ultrasound image) representing an internal state of the subject, based on a given frequency component in the second ultrasound signal coming from the inside of the subject in accordance with the first ultrasound signal and received by the receiving section 13. The examples of the given frequency component may include a fundamental wave component, and harmonic components such as a second-order harmonic component, a third-order harmonic component and a fourth-order harmonic component. The image processing section 14 may be configured to form an ultrasound image using a plurality of frequency components. For example, the image processing section 14 comprises: a DSP (Digital Signal Processor) configured to generate an ultrasound image of the subject, based on the output of the receiving section 13; and a digital-to-analog conversion circuit (DAC circuit) configured to convert a signal processed by the DSP from a digital signal to an analog signal in order to indicate the ultrasound image on the indicating section 15. For example, the DSP comprises a B-mode processing circuit, a Doppler processing circuit, and a color-mode processing circuit, and is capable of generating a so-called B-mode image, Doppler image and color-mode image.

The indicating section 15 is a device configured to, under control of the control section 16, indicate the ultrasound image of the subject generated by the image processing section 14. For example, the indicating section 15 is composed of a display such as a CRT display, an LCD (Liquid Crystal Display), an organic EL display, or a plasma display, or a printing unit such as a printer.

For example, the control section 16 is a circuit configured to comprise a microprocessor, a storage element, peripheral circuits thereof and others, and configured to control each of the manual operation input section 11, the sending section 12, the receiving section 13, the image processing section 14 and the indicating section 15 depending on a required function thereof to thereby perform overall control of the ultrasound diagnostic apparatus S.

As illustrated in FIG. 3, the ultrasound probe (transducer) 2 comprises a probe main unit 4, and an ultrasound transmitting-receiving section (piezoelectric device) 5 provided in the probe main unit 4 to perform transmitting and receiving of ultrasound. The ultrasound probe 2 will be described on an assumption that the direction X and the direction Y illustrated in FIG. 3 are, respectively, an upward direction and a downward direction. The same applies to FIGS. 6, 7 to 11, 13 and 16 described later.

The probe main unit 4 comprises a covering layer 41 provided at a front end thereof, a signal processing circuit section 42 provided at a rear end thereof 42, and a backing material layer 43 disposed between the covering layer 41 and the signal processing circuit section 42.

The covering layer 41 is configured to come into contact, for example, with a living body as a subject, during diagnosis, and made of a material, such as silicone rubber, which has a texture providing no uncomfortable feeling during the contact, and an acoustic impedance close to a human body in order to establish acoustic matching with a human body.

The backing material layer 43 fulfills a role of attenuating unwanted vibration occurring in the ultrasound transmitting-receiving section 5, or the like.

The signal processing circuit section 42 is connected to the ultrasound diagnostic apparatus S via the cable 3, and configured to perform a processing of generating a pulse signal for ultrasound transmitting, a processing for a receive pulse signal, or the like.

More specifically, the signal processing circuit section 42 is configured to, under control of the control section 16, supply a transmit signal sent from the sending section 12 in the form of an electric signal, to the ultrasound transmitting-receiving section 5 to thereby instruct the ultrasound transmitting-receiving section 5 to generate the first ultrasound signal. For example, it is configured to comprise a high-voltage pulse generator for generating a high-voltage pulse. The drive signal generated by the signal processing circuit section 42 is composed of a plurality of pulsed signals each having a delay time appropriately set for a respective one of aftermentioned elements 7 (see FIG. 4), wherein the plurality of pulsed signals are supplied, respectively, to diaphragms 6. Phases of ultrasounds emitted from the sets of diaphragms 6 according to the plurality of drive signals become coincident with each other in a specific direction (specific orientation) (or specific transmit focal point), and the first ultrasound signal is generated as a transmit beam having a main beam formed in the specific direction.

The signal processing circuit section 42 is further configured to, under control of the control section 16, receive a receive signal from the ultrasound transmitting-receiving section 5 in the form of an electric signal and process the receive signal. As with formation of the transmit beam during transmitting, a receive beam may be formed by performing so-called "phasing addition" during receiving. That is, a delay time is appropriately set for each of a plurality of output signals output, respectively, from the elements 7 each composed of the set of diaphragms 6 to allow phases of the output signals to become coincident with each other in a specific direction (specific orientation or specific receive focal point) when the plurality of mutually-delayed output signals are added together, to thereby form a main beam in the specific direction. In this case, for example, the signal processing circuit section 42 may further comprise a receive beam former configured to accept an input of the output signals after being amplified by the amplifier. The signal processing circuit section 42 may be appropriately modified. For example, it may be provided in the apparatus main unit 1.

Figure 4:
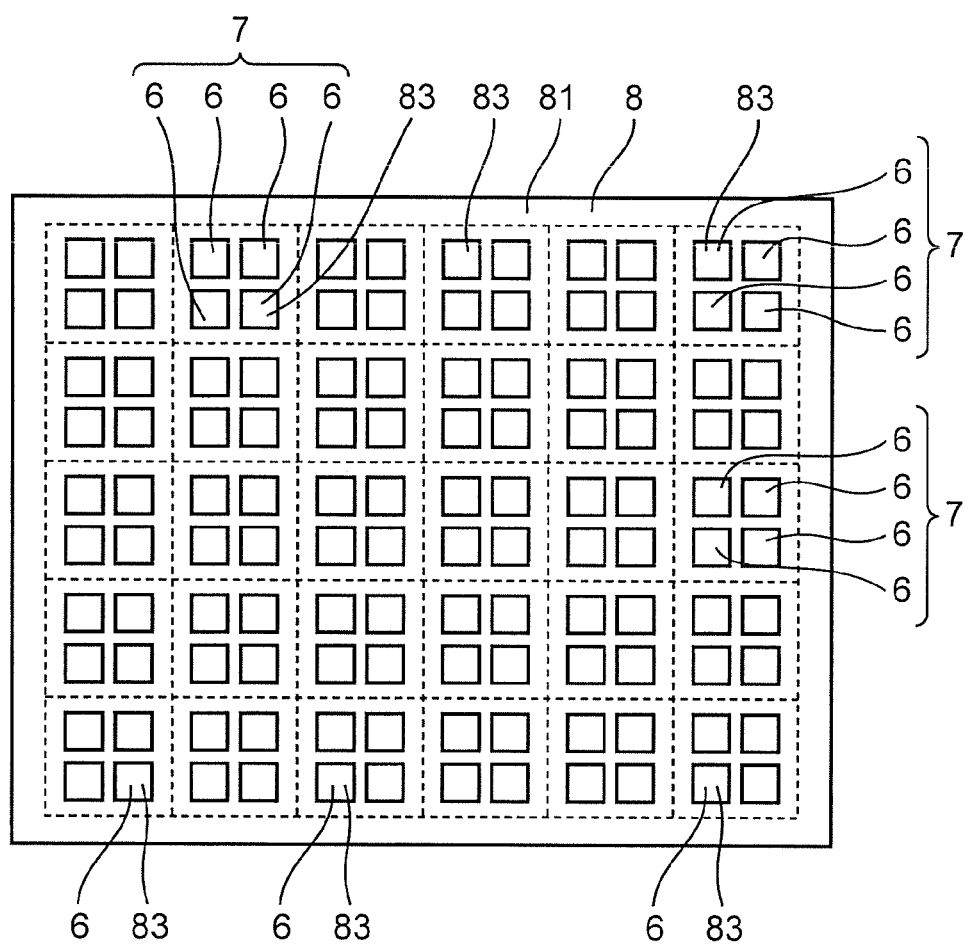
FIG. 4 is a back view illustrating an ultrasound transmitting-receiving section in the ultrasound probe.
Figure 5:
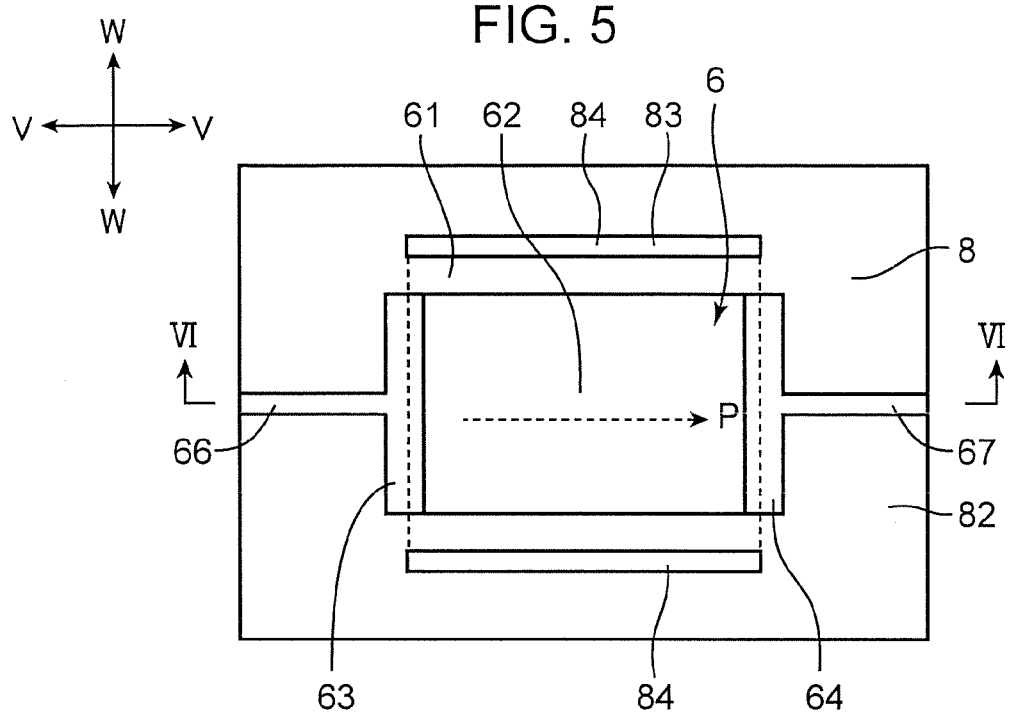
FIG. 5 is a fragmentary enlarged front view of the ultrasound transmitting-receiving section in the ultrasound probe.

The ultrasound transmitting-receiving section 5 is disposed between the covering layer 41 and the backing material layer 43 of the probe main unit 4. As illustrated in FIGS. 4 and 5, the ultrasound transmitting-receiving section 5 in this embodiment has a plurality of diaphragms 6, and a holding substrate 8 holding the diaphragms 6.

In this embodiment, the holding substrate 8 has a plate-shaped substrate body 81, and a sheet member 82 formed to have a thickness less than that of the substrate body 81 and laminated onto an upper surface of the substrate body 81.

Figure 6:
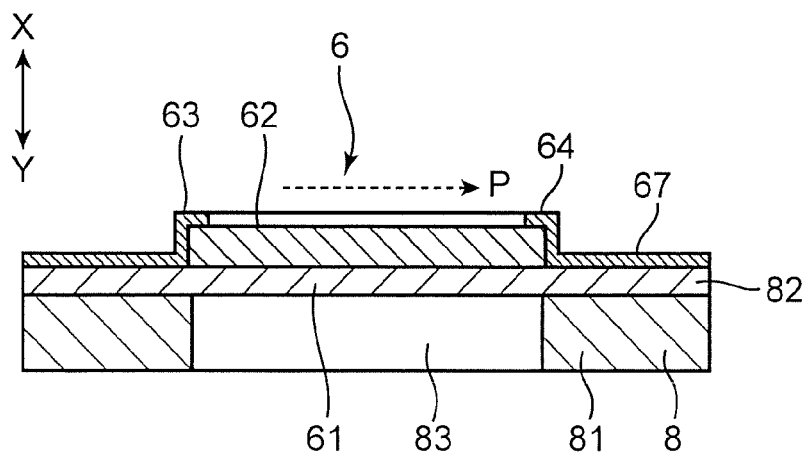
FIG. 6 is a sectional view taken along the line V1-V1 illustrated in FIG. 5.

The holding substrate 8 is provided with a plurality of approximately square-shaped recesses 83 arranged in a right-left direction and in a front-rear direction, as illustrated in FIG. 4. As illustrated in FIG. 6, each of the recesses 83 is formed to penetrate through the substrate body 81 so as to extend from a lower surface of the substrate body 81 to reach the sheet member 82 on the side of the upper surface thereof. As a result of formation of the recesses 83, a portion of the sheet member 82 located just above each of the recesses 83 and delimited by the recess 83 is formed as a membrane 61 having a thickness less than that of a region of the holding substrate 8 other than regions having the recesses 83.

Each of the diaphragms 6 has the membrane 61, a thin plate-shaped piezoelectric member 62 laminated onto an upper surface of the membrane 61 to form a unimorph structure in cooperation with the membrane 61, and a pair of electrodes 63, 64.

In this embodiment, in order to obtain an excellent potential distribution in an aftermentioned PZT-based piezoelectric member, the membrane 61 is made of an electrical insulating material such as silicon dioxide ($SiO_2$) or silicon nitride (SiN), and formed in a sheet shape (in this embodiment, thickness: about 2 μm).

Further, the membrane 61 in this embodiment is formed in a rectangular shape in which a width thereof in the front-rear direction (W-W direction) is less than a width of the recess 83 in the front-rear direction. That is, a slit 84 is formed in the membrane 61 in each of a region between a front edge of the membrane 61 and a front inner wall surface of the recess 83 and a region between a rear edge of the membrane 61 and a rear inner wall surface of the recess 83. Thus, the membrane 61 is held by the substrate body 81 along right and left opposite ends thereof.

The piezoelectric member 62 is made of a piezoelectric material. In this embodiment, the piezoelectric member 62 is made of PZT. However, the piezoelectric member 62 is not limited to a type made of PZT, but the material therefor may be appropriately modified. For example, the piezoelectric member may be made of quartz, lithium niobate ($LiNbO_3$), potassium tantalate niobate ($K(Ta, Nb)O_3$), barium titanate ($BaTiO_3$), lithium tantalate ($LiTaO_3$), strontium titanate ($SrTiO_3$), PZN-PT, PMN-PT, or the like.

In this embodiment, the piezoelectric member 62 has a rectangular shape with approximately the same size as that of the membrane 61, and a thickness, for example, of about 2 μm.

The piezoelectric member 62 is composed of a crystal having a single orientation (single-orientation crystal) in which crystallites thereof are arranged along the right-left direction, i.e., a first direction (V-V direction). The piezoelectric member 62 in this embodiment is a single-orientation crystal in which crystallites thereof are arranged along a direction perpendicular to the first direction, i.e., a second direction (W-W direction), in addition to the first direction. That is, the piezoelectric member 62 is a two-dimensionally oriented layer (two-dimensionally oriented plate shape), i.e., a layer (plate) oriented in two directions: the first direction; and the second direction linear independent of the first direction.

Figure 8A:
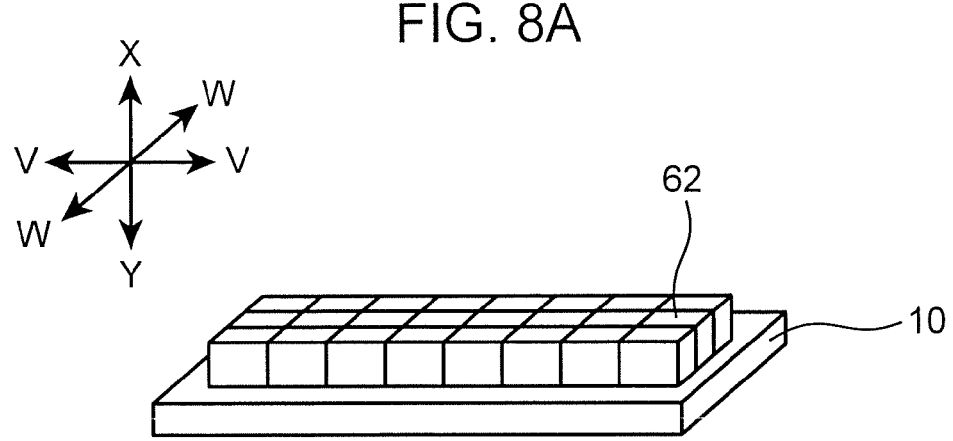
FIG. 8A is a perspective view schematically depicting a state in which a single-orientation piezoelectric member layer is formed on a single-crystal plate.

The above single-orientation piezoelectric member 62 can be obtained, for example, by epitaxially growing a piezoelectric member on a single-crystal layer, i.e., a layer of a single crystal (not illustrated), of a single-crystal plate 10, as illustrated in FIG. 8A.

Figure 8B:
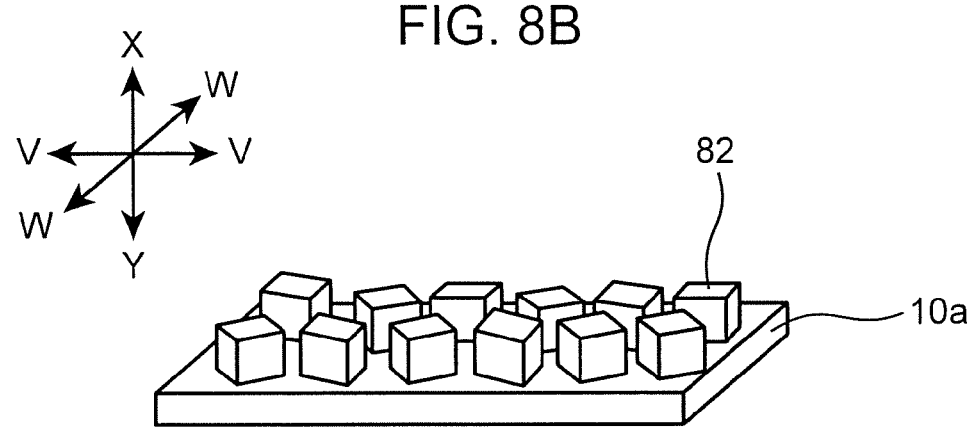
FIG. 8B is a perspective view schematically depicting a state in which a piezoelectric member layer is formed on substrate devoid of a single-crystal plate.
Figure 9:
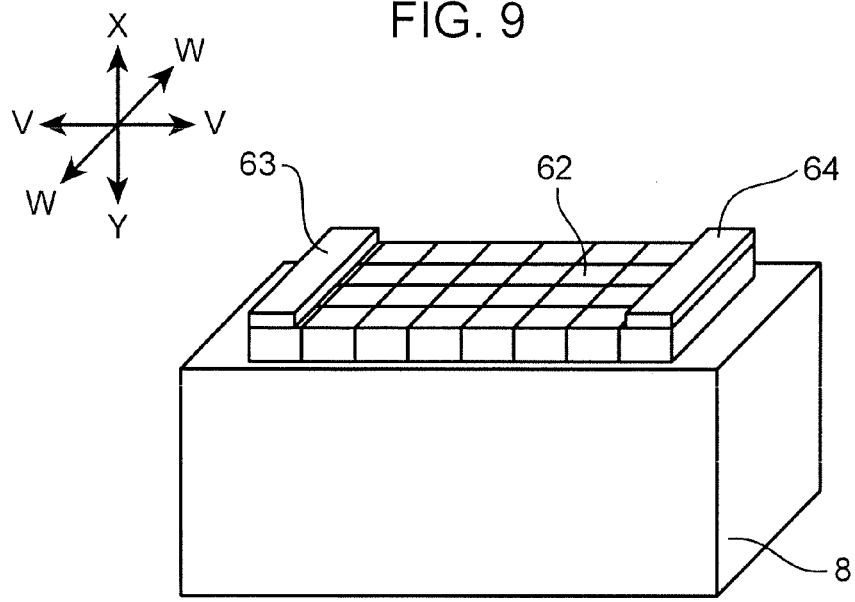
FIG. 9 is a perspective view schematically depicting a state in which electrodes are placed on a single-orientation piezoelectric member.

The single-crystal plate 10 is required to allow the piezoelectric member 62 to be epitaxially grown thereon. For this reason, it is necessary that lattice constants thereof are close to each other enough to achieve lattice matching. For example, if a substrate 10a for forming the piezoelectric member 62 thereon is devoid of a single-crystal layer, or if the above lattice constants fail to achieve lattice matching although the substrate 10a has a single-crystal layer, and thus the piezoelectric member 62 cannot be epitaxially grown, crystallites of the piezoelectric member 62 are randomly arranged, as illustrated in FIG. 8B, so that a single orientation is not obtained.

For example, in the case where PZT is used as a material for the piezoelectric member 62, as in this embodiment, MgO having a lattice constant (0.42 nm) close to a lattice constant (0.41 nm) of PZT as evidenced by Table 1 presenting lattice constants and others of a piezoelectric member and a single-crystal plate is suitably usable as a material for the single-crystal plate 10. Alternatively, in the case where PZT is used as a material for the piezoelectric member 62, $SrTiO_3$ (lattice constant: 0.39 nm) or $Al_2O_3$ (lattice constant: 0.48 nm) can also be used as a material for the single-crystal plate 10.

TABLE 1

| Material | | Linear coefficient of expansion (ppm/K) | Lattice constant (nm) |
|---|---|---|---|
| Piezoelectric member | PZT | 6.7 | 0.41 |
| Single-crystal plate | $Al_2O_3$ | 9.2 | 0.48 |
| | $SrTiO_3$ | 9.4 | 0.39 |
| | MgO | 11 | 0.42 |

As illustrated in FIGS. 5 and 6, the pair of electrodes are composed of a plus electrode 63 (first electrode) and a ground electrode 64 (second electrode).

The electrodes 63, 64 are made of gold, platinum or the like, and placed on an upper surface of the piezoelectric member 62, i.e., one of opposite surfaces thereof in its thickness direction, and a side surface of the piezoelectric member 62, with a given distance therebetween, in such a manner that each of them extends in a direction perpendicular to the thickness direction (X-Y direction) of the piezoelectric member 62 and in a direction (in this embodiment, W-W direction) perpendicular to the crystal orientation direction (in this embodiment, V-V direction) of the piezoelectric member 62.

More specifically, the plus electrode 63 is placed on a left edge of the upper surface of the piezoelectric member 62 to linearly extend over a given width in a direction from a front edge to a rear edge of the upper surface of the piezoelectric member 62. That is, the plus electrode 63 is placed on one of opposite edges of the upper surface of the piezoelectric member 62 in the first direction (V-V direction) to linearly extend over a given width in a direction from one edge to the other edge of the upper surface of the piezoelectric member 62 in the second direction (W-W direction).

On the other hand, the ground electrode 64 is placed on a right edge of the upper surface of the piezoelectric member 62 to linearly extend in parallel with the plus electrode 63 over the same width as that of the plus electrode 63 in the direction from the front edge to the rear edge of the upper surface of the piezoelectric member 62. That is, the ground electrode 64 is placed on the other edge of the upper surface of the piezoelectric member 62 in the first direction (V-V direction) to linearly extend over the given width in the direction from one edge to the other edge of the upper surface of the piezoelectric member 62 in the second direction. Thus, the plus electrode 63 and the ground electrode 64 are placed on the upper surface of the piezoelectric member 62 in parallel relation to each other with a given distance therebetween.

However, the arrangement of the electrodes 63, 64 are not limited to the above type in which each of them is placed on the upper surface and the side surface of the piezoelectric member 62, but may be appropriately modified. For example, the plus electrode 63 and the ground electrode 64 may be configured such that each of them is placed on only the upper surface of the piezoelectric member 62, or may be configured such that the plus electrode 63 is placed on only a left side surface of the piezoelectric member 62, and the ground electrode 64 is placed on only a right side surface of the piezoelectric member 62.

In this embodiment, the plurality of diaphragms 6 formed in the above manner are configured such that four of the diaphragms 6 (surrounded by the dashed line in FIG. 4) are mutually connected together to synchronously operate as one element 7, as illustrated in FIG. 4. Then, a plurality of the elements 7 are two-dimensionally arranged in the front-rear and right-left directions.

More specifically, the ground electrodes 64 each placed on a respective one of the four diaphragms 6 surrounded by the dashed line in FIG. 4 are connected to each other in an electrically conductable manner via a ground-electrode interconnection line 67 illustrated in FIG. 5, and then connected to the signal processing circuit section 42 via a penetration wiring or the like.

The plus electrodes 63 each placed on a respective one of the four diaphragms 6 surrounded by the dashed line in FIG. 4 are connected to each other in an electrically conductable manner via a plus-electrode interconnection line 66, and the plurality of elements 7 each consisting of the four diaphragms 6 are connected together by an element interconnection line (not illustrated) extending from the respective elements 7, and then connected to the signal processing circuit section 42 via a penetration wiring or the like.

First of all, as illustrated in FIG. 7A, by using a sputtering process, a piezoelectric member layer 62a is formed on a single crystal plate 10 made of MgO (100) having a thickness of about 300 μm, to have a thickness of about 2 μm. In place of the sputtering process, a film forming process may be a CVD process or a sol-gel process.

The formed piezoelectric member layer 62a is obtained through epitaxial growth on the single-crystal plate 10 to have a single orientation in which crystallites are arranged in the first direction (V-V direction) and in the second direction (W-W direction) as illustrated in FIG. 8A.

Subsequently, a holding substrate 8 comprising a substrate body 81 composed of a 200 μm-thick Si substrate and two sheet members 82, 82a each composed of a 2 μm-thick thermally-oxidized film and attached to a respective one of upper and lower surfaces of the substrate body 81 is prepared. In place of the thermally-oxidized film, a nitride film or the like may be formed.

Subsequently, as illustrated in FIG. 7B, the piezoelectric member layer 62a formed on the single-crystal plate 10 is positioned to face the sheet member 82, and, in this state, the piezoelectric member layer 62a and the sheet member 82 are bonded together by an adhesive or the like, so as to allow the piezoelectric member layer 62a to be held by the holding substrate 8.

The examples of the adhesive for bonding the piezoelectric member layer 62a and the sheet member 82 together include a polyimide-based adhesive, an epoxy-based adhesive and an acrylic-based adhesive. A method for bonding the piezoelectric member layer 62a and the sheet member 82 together may be appropriately modified and implemented. For example, the method may be resin bonding, SOG bonding, BCG bonding, or the like.

Subsequently, as illustrated in FIG. 7C, the single-crystal plate 10 composed of an MgO substrate is removed from the piezoelectric member layer 62a by using a heated aqueous solution of phosphoric acid, or the like.

Subsequently, as illustrated in FIG. 7D, a titanium film (20 nm) and a platinum film (100 nm) are sequentially formed on an upper surface of the piezoelectric member layer 62a by sputtering, to thereby form an electrode-forming layer 63a. The titanium film in the electrode-forming layer 63a serves as an adhesion layer, and the platinum film is formed as a plus electrode 63, a plus-electrode interconnection line 66, a ground electrode 64 and a ground-electrode interconnection line 67.

Subsequently, a photoresist is applied, and subjected to exposure and development. Then, the electrode-forming layer 63a consisting of the titanium and platinum films is etched by using a resulting resist pattern as a mask, so that the plus electrode 63 and the ground electrode 64 are formed as illustrated in FIG. 7E, and further the plus-electrode interconnection line 66 and the ground-electrode interconnection line 67 are formed although not illustrated in FIG. 7.

Subsequently, a resist pattern for patterning the piezoelectric member layer 62a is formed, and the piezoelectric member layer 62a is wet-etched by using fluonitric acid to form a plurality of rectangular-shaped piezoelectric members 62 are formed as illustrated in FIG. 7F (only one of them appears in FIG. 7F).

Subsequently, a photoresist is applied on the sheet member 82a on the side of the lower surface of the holding substrate, in a region thereof corresponding to each of the piezoelectric members 62, and subjected to exposure and development to form a resist pattern. Then, the sheet member 82a is dry-etched ($CHF_3$ gas) by an RIE apparatus to remove a portion of the sheet member 82a which is not protected by the resist.

This pattern corresponds to a deformable portion of a diaphragm. In this embodiment, it is formed as a rectangular pattern having a one-side length of 50 μm. Using the pattern of the sheet member 82a as a mask, the substrate body 81 is subjected to deep trenching by a Bosch process using an ICP apparatus, to form a recess 83. Thus, a portion of the sheet member 82 located just above the recess 83 and delimited by the recess 83 serves as a membrane 61, and each of front and rear end regions of the membrane 61 is cut to form a slit 84 (illustrated in FIG. 5A). In this way, a diaphragm 6 having a one-side length of about 50 μm is obtained.

Figure 10:
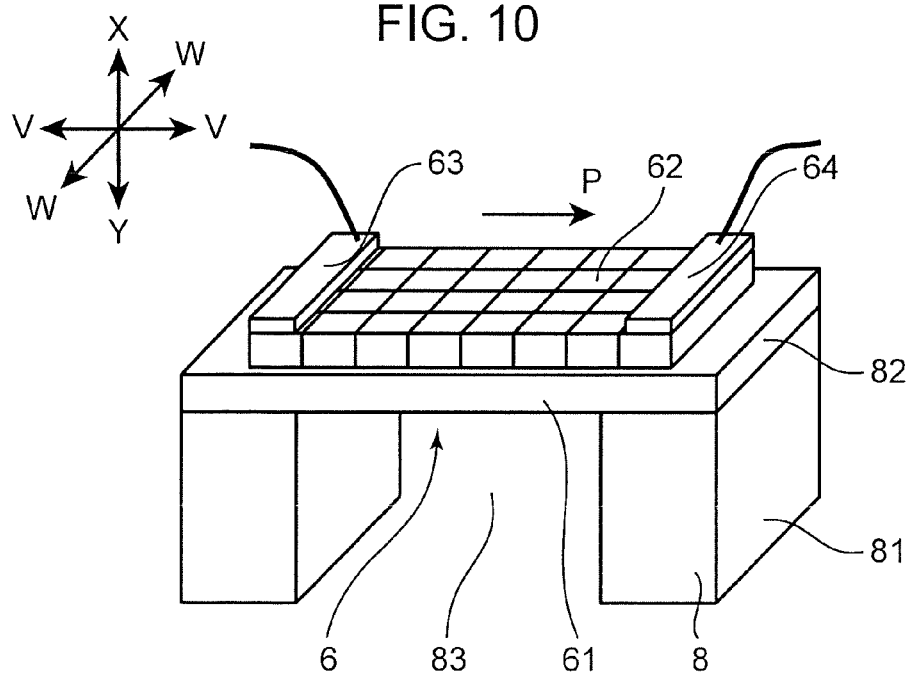
FIG. 10 is a perspective view schematically depicting a state in which a voltage is applied between the electrodes formed on the piezoelectric member to subject the piezoelectric member to a poling treatment.

Subsequently, as illustrated in FIG. 10, a voltage is applied between the plus electrode 63 and the ground electrode 64 in such a manner as to apply an electric field of several V/μm or more therebetween. In this way, the entire the piezoelectric member 62 is subjected to a poling treatment in a single direction P (poling direction) along the first direction (V-V direction) equal to the orientation direction.

In this embodiment, the piezoelectric member layer 62a and the sheet member 82 are bonded together by an adhesive, the piezoelectric member layer 62a is transferred to the holding substrate 8, and single-crystal plate 10 is removed from the piezoelectric member layer 62a. However, the present invention is not limited to using the transfer process. For example, a single-crystal plate composed of an MgO substrate may be directly used as a holding substrate 108.

More specifically, as illustrated in FIG. 11A, the holding substrate 108 is composed of an MgO single-crystal plate, and a piezoelectric member layer is formed on an upper surface of the holding substrate 108, i.e., one of opposite surfaces thereof in its thickness direction, by a film forming process, and processed to form a piezoelectric member 62. Further, a plus electrode 63, a plus-electrode interconnection line 66, a ground electrode 64 and a ground-electrode interconnection line 67 are formed, and a recess 183 is formed in a lower surface, i.e., the other surface in the thickness direction to extend from the lower surface toward the upper surface so as to have a given depth.

This recess 183 is formed, for example, by masking the lower surface using a mask member composed of a photoresist, and performing etching using a heated aqueous solution of phosphoric acid having a concentration of 40%, at 80° C.

Alternatively, as illustrated in FIG. 11B, a single-crystal layer 10b is formed on a holding substrate 108a composed of a Si substrate, and a piezoelectric member 62 is formed on the single-crystal layer 10b. Then, a recess 183a may be formed in a lower surface of the holding substrate 108a. In this case, a method for forming the single-crystal layer 10b includes: depositing a single-crystal layer on the holding substrate 108a by sputtering or the like; and bonding a single-crystal layer on the holding substrate 108a (and then, when the bonded single-crystal layer 10b is excessively thick, grinding the single-crystal layer to adjust a thickness thereof).

In diagnosis using the ultrasound diagnostic apparatus S having the ultrasound probe 2 configured as above, for example, when an instruction on start of the diagnosis is input through the manual operation input section 11, the signal processing circuit section 42 generates a pulse signal for ultrasound transmitting, under control of the control section 16.

According to this generated pulse signal, a pulse voltage is applied between the plus electrode 63 and the ground electrode 64 in each of the plurality of elements 7 (each composed of the four diaphragms 6) of the ultrasound transmitting-receiving section 5, with a given delay time, to form an electric field in a direction perpendicular to the thickness direction of the piezoelectric member 62.

Due to this electric field, each of the piezoelectric members 62 is strained in the direction perpendicular to the thickness direction by a piezoelectric effect. In this process, the piezoelectric member 62 is efficiently strained, because the orientation direction thereof and the poling direction are coincident with each other to thereby obtain excellent piezoelectric properties.

Due to the strain in each of the piezoelectric members 62, the corresponding diaphragm 6 is bendingly deformed in a curved shape upwardly in an up-down direction, i.e., in the thickness direction. Then, the diaphragm 6 being bendingly deformed is vibrated according to resonant properties (resonant frequency and attenuation property) thereof, and therefore pulse ultrasound is transmitted toward an inside of a living body. Phases of arrays of the elements 7 are shifted step-by-step by a given value to thereby focus and steer (directionally control) an ultrasound beam to three-dimensionally scan a required region. Within the living body, ultrasound is transmitted while being attenuated, and reflection occurs in a region causing a difference in acoustic impedance, so that the reflected ultrasound is returned to the ultrasound probe 2.

Each of the diaphragms 6 is vibrated by the returned ultrasound, and electric charges are generated in the plus electrode 63 according to a resulting strain in the corresponding piezoelectric member 62.

Then, the signal processing circuit section 42 processes the generated electric charges and outputs a receive signal to the image processing section 14. Then, under control of the control section 16 and based on the received receive signal, the image processing section 14 detects a distance to a subject, from a period of time from transmitting to receiving, and a direction of the subject, from a time lag between the elements, to generate an ultrasound image of the subject. The image processing section 14 further extracts harmonic components from the receive signal by a filter method, and generates an ultrasound image representing an internal state of the subject based on the extracted harmonic components by using a harmonic imaging technique. Alternatively, for example, the image processing section 14 extracts harmonic components from the receive signal by a phase inversion method (pulse inversion method), and generates an ultrasound image representing an internal state of the subject based on the extracted harmonic components by using a harmonic imaging technique. Then, under control of the control section 16, the indicating section 15 indicates an ultrasound image of the subject generated by the image processing section 14.

In the above embodiment, the ultrasound probe 2 is configured to comprise one set of the two electrodes: the plus electrode 63 disposed on the left edge side of the piezoelectric member 62; and the ground electrode 64 disposed on the right edge side of the piezoelectric member 62. However, the ultrasound probe 2 is not limited to the configuration in this embodiment, but may be appropriately modified. For example, it may be configured to comprise a plurality of sets of a plus electrode and a ground electrode.

Figure 12:
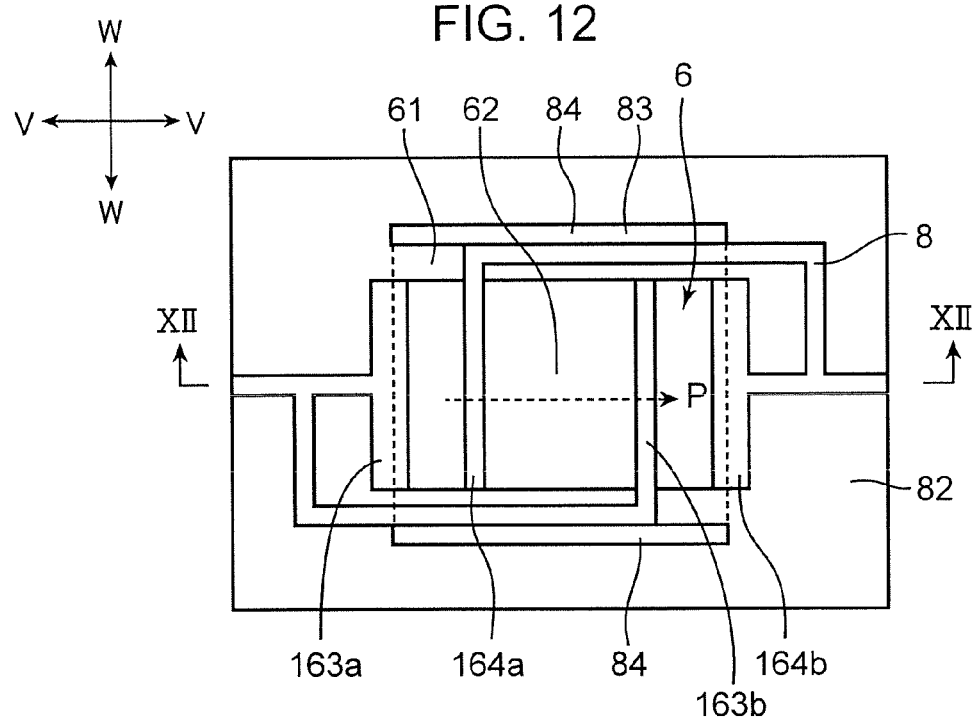
FIG. 12 is a fragmentary enlarged front view of a third example of the modification of the ultrasound transmitting-receiving section.
Figure 13:
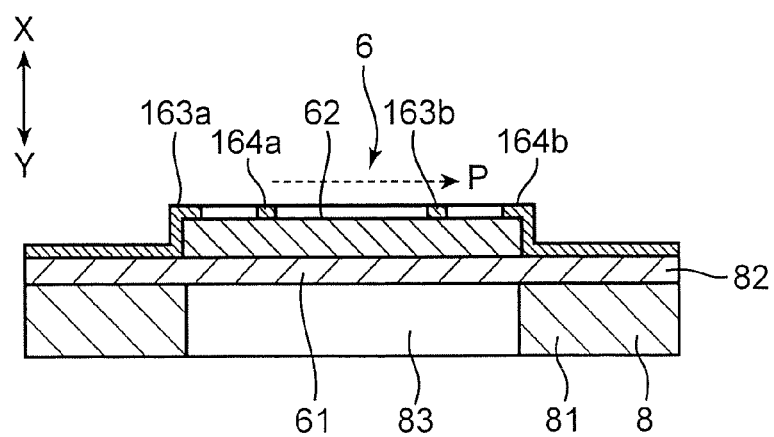
FIG. 13 is a sectional view taken along the line XII-XII illustrated in FIG. 12.

More specifically, as illustrated in FIGS. 12 and 13, the plus electrode is composed of a first set-constituting plus electrode 163a, and a second set-constituting plus electrode 163b, and the ground electrode is composed of a first set-constituting ground electrode 164a, and a second set-constituting ground electrode 164b.

The first set-constituting plus electrode 163a is disposed on the left edge side of the upper surface of the piezoelectric member 62 to extend along the front-rear direction. The second set-constituting plus electrode 163*b* is placed on the upper surface of the piezoelectric member 62 at a position rightward of the first set-constituting plus electrode 163*a*, in parallel relation to the first set-constituting plus electrode 163*a* with a given distance therebetween, and mutually connected with the first set-constituting plus electrode 163*a*.

The first set-constituting ground electrode 164*a* is placed on the upper surface of the piezoelectric member 62 at a position between the first set-constituting plus electrode 163*a* and the second set-constituting plus electrode 163*b*, in parallel relation to the first set-constituting plus electrode 163*a* with a given distance therebetween. The second set-constituting ground electrode 164*b* is placed on the right edge of the upper surface of the piezoelectric member 62 at a position rightward of the second set-constituting plus electrode 163*b*, in parallel relation to the second set-constituting plus electrode 163*b* with a given distance therebetween, and mutually connected with the first set-constituting ground electrode 164*a*.

This configuration makes it possible to allow the piezoelectric member 62 to be strained by a lower voltage and thus more efficiently strained.

In this case, for example, a poling treatment for an unpoled piezoelectric member 62 is performed, for example, by applying a voltage between the first set-constituting plus electrode 163*a* before being mutually connected with the second set-constituting plus electrode 163*b*, and the second set-constituting ground electrode 164*b* before being mutually connected with the first set-constituting ground electrode 164*a*, so as to apply an electric field of several V/µm therebetween, to thereby subject the entire unpoled piezoelectric member 62 to poling in the single direction P (poling direction) along the first direction (V-V direction) equal to the orientation direction.

In the above embodiment, the ultrasound probe 2 is configured to comprise one set of the two electrodes: the plus electrode 63 disposed on the left edge side of the piezoelectric member 62; and the ground electrode 64 disposed on the right edge side of the piezoelectric member 62. In place of or in addition to this configuration, an additional pair of electrodes may be provided on a sidewall of the piezoelectric member 62.

Figure 14:
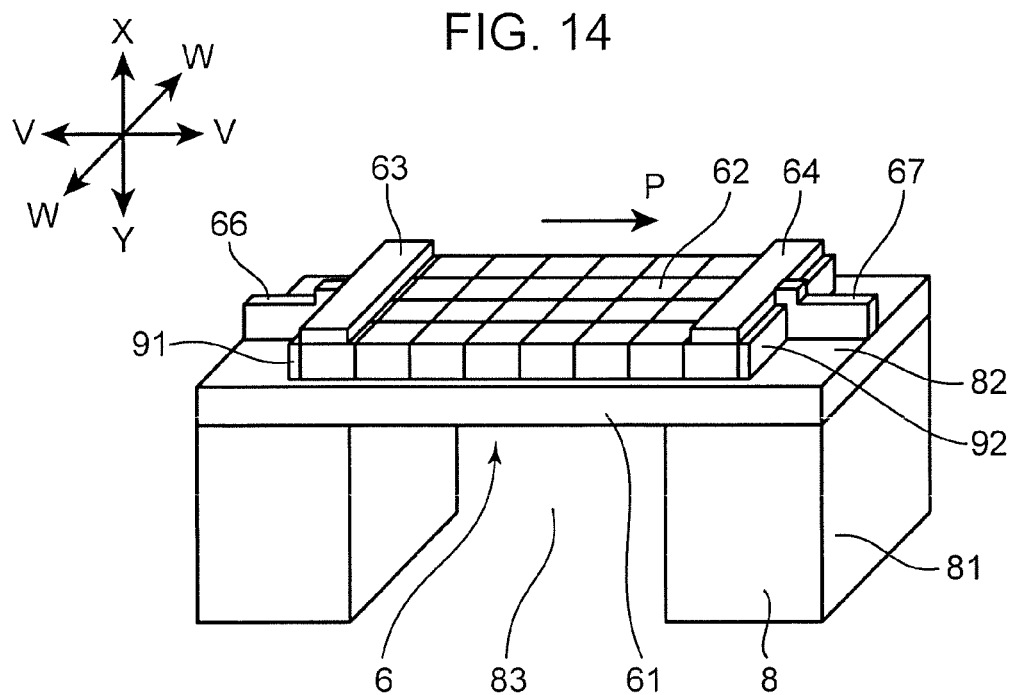
FIG. 14 is a fragmentary enlarged perspective view of a fourth example of the modification of the ultrasound transmitting-receiving section.
Figure 15:
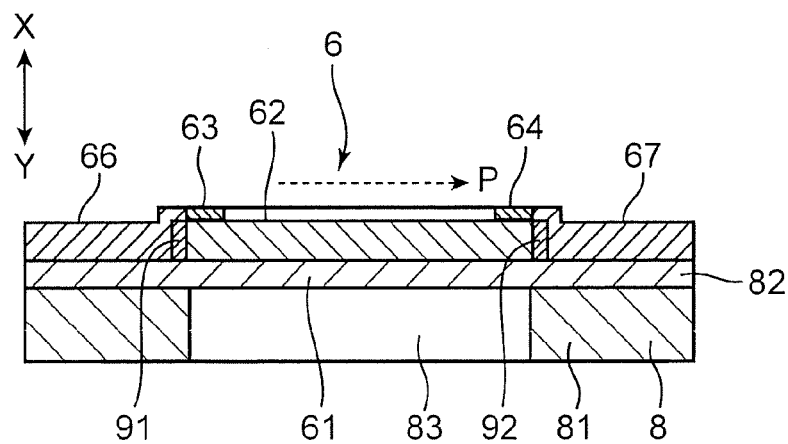
FIG. 15 is a fragmentary sectional view of the fourth example of the modification of the ultrasound transmitting-receiving section, illustrated in FIG. 14.
Figure 16:
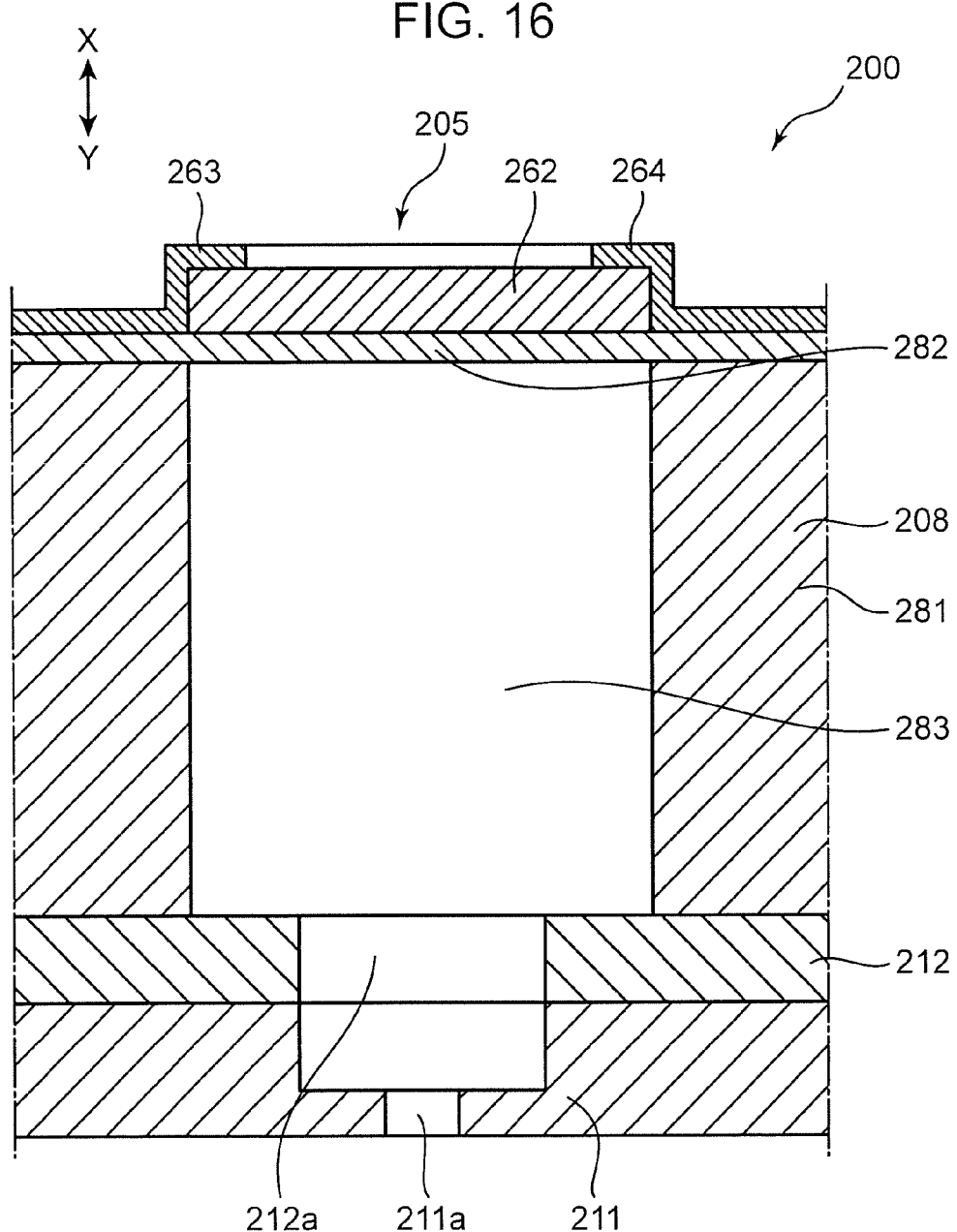
FIG. 16 is a fragmentary sectional view of a droplet discharge unit according to a second embodiment of the present invention.
Figure 17:
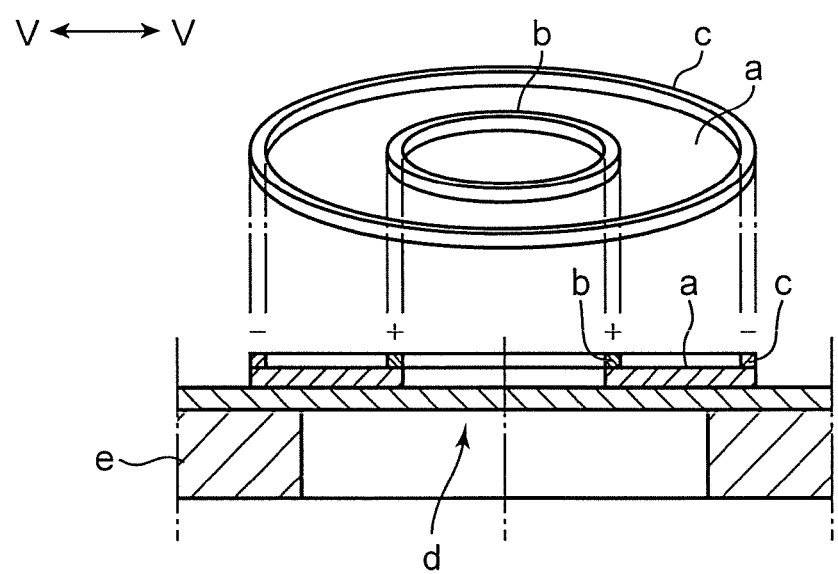
FIG. 17 is an explanatory diagram of a conventional example of an ultrasound transmitting-receiving section of an ultrasound probe.

FIG. 14 is a fragmentary enlarged perspective view of a fourth example of modification of the ultrasound transmitting-receiving section. FIG. 15 is a fragmentary sectional view of the fourth example of the modification of the ultrasound transmitting-receiving section, illustrated in FIG. 14.

FIGS. 14 and 15 illustrate a configuration in which an additional pair of electrodes 91, 92 are provided on the sidewall of the piezoelectric member 62, in addition to the plus electrode 63 and the ground electrode 64. In the fourth example illustrated in FIGS. 14 and 15, an ultrasound probe 2 additionally has one set of two electrodes: a plus electrode 91 placed on a left side surface (left sidewall) of the piezoelectric member 62 to extend along the thickness direction and a direction perpendicular to the orientation direction; and a ground electrode 92 placed on a right side surface (right sidewall) of the piezoelectric member 62 to extend along the thickness direction and a direction perpendicular to the orientation direction. In FIGS. 14 and 15, the part of the electrodes 63, 64 may be omitted.

As above, the ultrasound transmitting-receiving section (piezoelectric device) provided in the probe body to perform transmitting and receiving of ultrasound comprises: the plate-shaped piezoelectric member 62; and the pair of first and second electrodes 91, 92 configured to apply a voltage across the piezoelectric member 62, wherein the piezoelectric member 62 has a single orientation in a direction (V-V direction) perpendicular to the thickness direction (X-Y direction) thereof; and each of the pair of first and second electrodes 91, 92 is placed to extend in a direction along the thickness direction (X-Y direction) and in a direction (W-W direction) perpendicular to the direction of the orientation.

In this configuration, an electric field is more likely to be generated in a direction perpendicular to the thickness direction of the piezoelectric member 62, so that the orientation direction is more exactly coincident with a poling direction.

In the above embodiment, the piezoelectric device is used for the ultrasound probe 2. However, the application of the piezoelectric device is not limited thereto, but the piezoelectric device may also be used for a droplet discharge unit 200 for discharging droplets such as ink droplets, e.g., for a printer (not illustrated). A droplet discharge unit 200 using a piezoelectric device in a discharge actuating section 205 will be described based on FIG. 16.

The droplet discharge unit 200 has a discharge actuating section 205 and a nozzle plate 211. The discharge actuating section 205 has a piezoelectric member 262, a plus electrode 263 placed on an upper surface of the piezoelectric member 262 at a position on a left edge side of the upper surface, a ground electrode 264 placed on the upper surface of the piezoelectric member 262 at a position on a right edge side of the upper surface, and a holding member 208 holding the above components.

The piezoelectric member 262, the piezoelectric member 263 and the ground electrode 264 are structurally the same as the corresponding components in the aforementioned embodiment.

The holding member 208 is approximately structurally the same as the corresponding components in the aforementioned first embodiment, wherein a recess formed in a substrate body 281 is used as a pressure chamber 283, and a sheet member forming an inner upper wall of the pressure chamber 283 makes up a membrane 282 exposed to an inside of the pressure chamber 283. In the second embodiment, the membrane 282 is devoid of the slits 86 provided in the aforementioned embodiment.

The nozzle plate 211 is formed by bonding it to a lower surface of the substrate body 281 through a glass substrate 212 using anodic bonding or the like.

The glass substrate 212 has an ink-discharging hole 212*a* penetratingly formed to communicate with the pressure chamber 283. Further, the nozzle plate 211 has a nozzle 211*a* penetratingly formed as an ink-discharging two-step hole communicating with the hole 212*a*. As a material for the nozzle plate 212, it is possible to use Si, glass, polyimide, photosensitive resin or the like.

The droplet discharge unit 200 prepared in the above manner is attached, for example, to a printer body (not illustrated), and an ink tank (not illustrated) is attached to the discharge actuating section 205. The discharge actuating section 205 and the ink tank (not illustrated) connect to each other via an ink flow passage.

In the droplet discharge unit 200 configured as above, upon applying a given voltage across the piezoelectric member 262, the piezoelectric member 262 is strained and deformed, and, accordingly, the entire diagram is deformed like a drumhead, so that ink in the pressure chamber 283 is discharged from the nozzle 211*a*.

This specification discloses techniques having various aspects, as mentioned above. Among them, major techniques will be outlined below.

According to one aspect, there is provided a piezoelectric device which comprises: a plate-shaped piezoelectric member; and a pair of first and second electrodes configured to apply a voltage across the piezoelectric member, wherein the piezoelectric member has a single orientation in a direction perpendicular to a thickness direction thereof, and each of the pair of first and second electrodes is placed to extend in a direction perpendicular to the thickness direction and in a direction perpendicular to the direction of the orientation.

In this piezoelectric device, each of the pair of first and second electrodes is placed to extend in a direction perpendicular to the thickness direction and in a direction perpendicular to the direction of the orientation. Thus, in this piezoelectric device, a poling treatment for the piezoelectric member can be performed by applying a voltage between the first electrode and the second electrode. This allows a poling direction and the orientation direction to become coincident with each other, thereby obtaining excellent piezoelectric properties.

According to another aspect, the above piezoelectric device further comprises: a single-crystal layer which is a layer of a single-crystalline material; and a plate-shaped holding substrate holding the piezoelectric member in such a manner as to allow the piezoelectric member to be epitaxially grown on the single-crystal layer.

The piezoelectric device having this feature makes it possible to allow the piezoelectric member to be easily obtained with a single orientation in a direction perpendicular to the thickness direction.

According to another aspect, in the above piezoelectric device, the single-crystal layer is formed in a single-crystal plate which is provided independently of the holding substrate, wherein the piezoelectric member formed using the single-crystal plate is held by the holding substrate.

According to this feature, the single-crystal layer for epitaxially growing the piezoelectric member thereon and the holding substrate holding the piezoelectric member in the piezoelectric device are composed, respectively, of independent components. Therefore, in the piezoelectric device having this feature, as a material for the holding substrate, it is possible to use the same material as that for a holding substrate in a conventional piezoelectric device. Thus, the piezoelectric device having this feature makes it possible to perform processing of the holding substrate using a conventional processing technique for the holding substrate made of the material, thereby enhancing producibility.

According to another aspect, the above piezoelectric device further comprises one or more pairs of additional first and second electrodes.

The piezoelectric device having this feature makes it possible to allow the piezoelectric member to be strained by a lower voltage and thus more efficiently strained.

According to another aspect, there is provided an ultrasound probe comprising any one of the above piezoelectric devices.

This ultrasound probe can efficiently transmit and receive ultrasound by the above piezoelectric device having excellent piezoelectric properties.

According to another aspect, there is provided a droplet discharge unit comprising any one of the above piezoelectric devices.

This droplet discharge unit efficiently can discharge droplets by the above piezoelectric device having excellent piezoelectric properties.

According to another aspect, there is provided a piezoelectric device which comprises: a plate-shaped piezoelectric member; and a pair of first and second electrodes configured to apply a voltage across the piezoelectric member, wherein the piezoelectric member has a single orientation in a direction perpendicular to a thickness direction thereof, and each of the pair of first and second electrodes is placed to extend in a direction along the thickness direction and in a direction perpendicular to the direction of the orientation.

In this piezoelectric device, an electric field is more likely to be generated in a direction perpendicular to the thickness direction of the piezoelectric member, so that the orientation direction is more exactly coincident with the poling direction.

According to another aspect, there is provided a piezoelectric device fabrication method (production method) for fabricating (producing) a piezoelectric device which comprises a plate-shaped piezoelectric member and a pair of first and second electrodes configured to apply a voltage across the piezoelectric member. The method comprises the steps of: forming a piezoelectric member having a single orientation in a direction perpendicular to a thickness direction thereof; and placing each of the pair of first and second electrodes in such a manner as to extend in a direction perpendicular to the thickness direction and in a direction perpendicular to the direction of the orientation.

In this piezoelectric device fabrication method, a poling treatment can be performed by applying a voltage between the first electrode and the second electrode. This allows the poling direction and the orientation direction to become coincident with each other, thereby obtaining excellent piezoelectric properties and facilitating poling of the piezoelectric member.

According to another aspect, the above piezoelectric device fabrication method further comprises the step of holding the piezoelectric member by a plate-shaped holding substrate in such a manner as to allow the piezoelectric member to be epitaxially grown on the single-crystal layer.

The piezoelectric device fabrication method having this feature makes it possible to allow the piezoelectric member to be easily produced with a single orientation in a direction perpendicular to the thickness direction.

According to another aspect, the above piezoelectric device fabrication method comprises the steps of: forming the piezoelectric member using a single-crystal plate which is provided independently of the holding substrate and having the single-crystal layer; and holding the piezoelectric member formed using the single-crystal plate, by the holding substrate.

In the piezoelectric device fabrication method having this feature, as a material for the holding substrate, it is possible to use the same material as that for a holding substrate in a conventional piezoelectric device, so that the piezoelectric device fabrication method having this feature makes it possible to process the holding substrate using a conventional processing technique for the holding substrate made of the material, thereby enhancing producibility.

This application is based on Japanese Patent Application Serial No. 2012-51349 filed in Japan Patent Office on Mar. 8, 2012, the contents of which are hereby incorporated by reference.

Although the present invention has been illustrated and described adequately and fully by way of example with reference to the accompanying drawings in order to represent the present invention, it is to be understood that various changes and modifications will be apparent to those skilled in the art. Therefore, unless otherwise such changes and modifications depart from the scope of the present invention hereinafter defined, they should be construed as being included therein.

INDUSTRIAL APPLICABILITY

The present invention can provide a piezoelectric device, a fabrication method for the piezoelectric device, and an ultrasound probe and a droplet discharge unit each using the piezoelectric device.

The invention claimed is:

1. A piezoelectric device comprising:
    a single-crystal layer which is a layer of a single-crystalline material;
    a plate-shaped piezoelectric member formed on the single-crystal layer;
    a pair of first and second electrodes configured to apply a voltage across the piezoelectric member; and
    a plate-shaped holding substrate holding the single-crystalline material,
    wherein the piezoelectric member has a single orientation in a direction perpendicular to a thickness direction thereof; and
    wherein each of the pair of first and second electrodes is placed to extend in a direction perpendicular to the thickness direction and in a direction perpendicular to the direction of the orientation.

2. The piezoelectric device according to claim 1, wherein the single-crystal layer is formed in a single-crystal plate which is provided independently of the holding substrate.

3. The piezoelectric device according to claim 1, further comprising one or more pairs of additional first and second electrodes.

4. An ultrasound probe comprising the piezoelectric device according to claim 1.

5. A droplet discharge unit comprising the piezoelectric device according to claim 1.

6. The piezoelectric device according to claim 1, wherein the pair of first and second electrodes is configured so that a sufficient voltage can be applied to deform the piezoelectric member.

7. A piezoelectric device comprising:
    a single-crystal layer which is a layer of a single-crystalline material;
    a plate-shaped piezoelectric member formed on the single-crystal layer;
    a pair of first and second electrodes configured to apply a voltage across the piezoelectric member; and
    a plate-shaped holding substrate holding the single-crystalline material,
    wherein the piezoelectric member has a single orientation in a direction perpendicular to a thickness direction thereof; and
    wherein each of the pair of first and second electrodes is placed to extend in a direction along the thickness direction and in a direction perpendicular to the direction of the orientation.

8. The piezoelectric device according to claim 1, comprising a plurality of sets of first and second electrodes.

9. The piezoelectric device according to claim 8, wherein the first and second electrodes in each of the sets are placed with a given distance there between in the direction of orientation.

10. The piezoelectric device according to claim 8, wherein the first and second electrodes in the sets are respectively configured so that sufficient voltages can be applied to deform the piezoelectric member.

11. The piezoelectric device according to claim 8, wherein the first electrodes in the sets are mutually connected with each other, and the second electrodes in the sets are mutually connected with each other.

12. The piezoelectric device according to claim 1, wherein the piezoelectric member has a poling direction which is parallel to a direction of an electrical field applied to the piezoelectric member to deform the piezoelectric member.

13. The piezoelectric device according to claim 7, wherein the pair of first and second electrodes is configured so that a sufficient voltage can be applied to deform the piezoelectric member.

14. The piezoelectric device according to claim 7, comprising a plurality of sets of first and second electrodes.

15. The piezoelectric device according to claim 7, wherein the piezoelectric member has a poling direction which is parallel to a direction of an electrical field applied to the piezoelectric member to deform the piezoelectric member.

16. A piezoelectric device fabrication method for fabricating a piezoelectric device which comprises a plate-shaped piezoelectric member and a pair of first and second electrodes configured to apply a voltage across the piezoelectric member, comprising the steps of:
    forming a piezoelectric member having a single orientation in a direction perpendicular to a thickness direction thereof;
    placing each of the pair of first and second electrodes in such a manner as to extend in a direction perpendicular to the thickness direction and in a direction perpendicular to the direction of the orientation; and
    holding the piezoelectric member by a plate-shaped holding substrate in such a manner as to allow the piezoelectric member to be epitaxially grown on a single-crystal layer.

17. The piezoelectric device fabrication method according to claim 16, further comprising the steps of:
    forming the piezoelectric member using a single-crystal plate which is provided independently of the holding substrate and having the single crystal layer; and
    holding the piezoelectric member formed using the single-crystal plate, by the holding substrate.

* * * * *